US008577697B2

(12) United States Patent
Demopulos

(10) Patent No.: US 8,577,697 B2
(45) Date of Patent: Nov. 5, 2013

(54) USE OF INTERNET SITE AS A REGISTRY FOR RESULTS OF MEDICAL TESTS

(76) Inventor: Gregory A. Demopulos, Mercer Island, WA (US)

(*) Notice: Subject to any disclaimer, the term of this patent is extended or adjusted under 35 U.S.C. 154(b) by 0 days.

(21) Appl. No.: 12/767,752

(22) Filed: Apr. 26, 2010

(65) Prior Publication Data

US 2010/0318379 A1  Dec. 16, 2010

Related U.S. Application Data

(63) Continuation of application No. 09/566,530, filed on May 8, 2000, now abandoned.

(60) Provisional application No. 60/185,562, filed on Feb. 28, 2000.

(51) Int. Cl.
*G06Q 50/00* (2012.01)
*G06Q 10/00* (2012.01)

(52) U.S. Cl.
USPC .................................................. 705/3; 705/2

(58) Field of Classification Search
USPC ............................................................ 705/3
See application file for complete search history.

(56) References Cited

U.S. PATENT DOCUMENTS

| 4,315,309 | A | | 2/1982 | Coli |
| 5,325,294 | A | * | 6/1994 | Keene ................................ 705/3 |
| 5,576,952 | A | | 11/1996 | Stutman et al. |
| 5,612,870 | A | | 3/1997 | Welner |
| 5,772,585 | A | | 6/1998 | Lavin et al. |
| 5,815,252 | A | | 9/1998 | Price-Francis |
| 5,867,688 | A | | 2/1999 | Simmon |
| 5,876,926 | A | * | 3/1999 | Beecham ................................ 435/5 |
| 5,897,989 | A | | 4/1999 | Beecham |

(Continued)

FOREIGN PATENT DOCUMENTS

| JP | 09311902 | 12/1997 |
| JP | 10-508970 | 9/1998 |

(Continued)

OTHER PUBLICATIONS

Department of Veterans Affairs, Radiology / Nuclear Medicine Release Notes, Apr. 1998, Version 5.0.*
Batz, E.B., Will your Business Model Float?, Oct. 1996, Pages pp. 1-11.
Brochure from eScreen, 2002, pp. 8.

(Continued)

*Primary Examiner* — Tran Nguyen
(74) *Attorney, Agent, or Firm* — Knobbe Martens Olson & Bear LLP

(57) ABSTRACT

Results of medical tests for sexually transmissible diseases (STDs) or other medical conditions such as drug use are posted to a registry site accessible by a subscriber and any authorized guest of the subscriber. The medical test results are associated with a verification of the subscriber's identity. The verification may be in the form of a driver's license number, or other indicia of identification, recorded when a test sample was drawn by a testing lab affiliated with the registry site. Results of the test performed by the testing lab are automatically posted to the registry site, along with the customer ID assigned to the subscriber when registering with the registry site, and the verification of the subscriber's identity. Subsequently, the subscriber and any authorized guest or prospective sexual partner can access the subscriber's test results and the verification of the subscriber's identity by entering a predefined password or other access code, thereby enabling the guest, who may be a prospective sexual partner, to verify a medical condition asserted by the subscriber.

29 Claims, 6 Drawing Sheets

(56) References Cited

U.S. PATENT DOCUMENTS

| | | | |
|---|---|---|---|
| 5,924,074 A | 7/1999 | Evans | |
| 5,987,440 A * | 11/1999 | O'Neil et al. | 705/44 |
| 6,018,713 A * | 1/2000 | Coli et al. | 705/2 |
| 6,032,119 A | 2/2000 | Brown et al. | |
| 6,044,353 A | 3/2000 | Pugliese, III | |
| 6,073,106 A | 6/2000 | Rozen et al. | |
| 6,226,378 B1 | 5/2001 | Quattrocchi | |
| 6,376,251 B1 | 4/2002 | Braun | |
| 6,438,601 B1 | 8/2002 | Hardy | |
| 6,463,417 B1 * | 10/2002 | Schoenberg | 705/2 |
| 6,581,012 B1 | 6/2003 | Aryev | |
| 6,695,203 B2 | 2/2004 | Iki et al. | |
| 6,698,653 B1 | 3/2004 | Diamond et al. | |
| 2004/0111297 A1 * | 6/2004 | Schoenberg | 705/3 |

FOREIGN PATENT DOCUMENTS

| | | |
|---|---|---|
| JP | 11149504 | 6/1999 |
| JP | 11-250165 | 9/1999 |
| KR | 1999-017304 | 3/1999 |
| WO | WO 98/32076 | 7/1998 |
| WO | WO 99/04043 | 1/1999 |

OTHER PUBLICATIONS eScreen News: eScreen, Inc. introduces MyeScreen.com, a Web-based Reporting Solution for the Drug-Testing industry, eScreen, 2001, pp. 2.

Hrobjartur, Jonatanson, Iceland's health sector database: A significant head start in the search for biological grail or an irreversible error?, American Journal of Law and Medicine, 2000, vol. 26, Issue 1, pp. 31-67.

Jonatansson, Hrobjartur, Iceland's health sector database: A significant head start in the search for biological grail or an irreversible error?, American Journal of Law and Medicine, 2000, vol. 26, Issue 1, pp. 31-67, Boston.

Raghupathi, et al., Strategic uses of information technology in health care: A state-of-the-art survey, Topics in Health Information Management, Aug. 1999, vol. 20, Issue 1, pp. 1-14.

Weber, David O., Web sites of tomorrow: How the Internet will transform healthcare, Health Forum Journal, May/Jun. 1999, vol. 42, Issue 3, pp. 40-45, San Francisco, CA.

Wullianallur et al., Strategic uses of information technology in health care: A state-of-the-art survey, Topics in Health Information Management, Aug. 1999, vol. 20, Issue 1, pp. 1.

* cited by examiner

USE OF INTERNET SITE AS A REGISTRY FOR RESULTS OF MEDICAL TESTS

RELATED PATENT APPLICATION

This application is a continuation of U.S. application Ser. No. 09/566,530, filed on May 8, 2000, which claims the benefit of U.S. provisional patent application, Ser. No. 60/185,562, filed Feb. 28, 2000, the benefit of the filing date of which is hereby claimed under 35 U.S.C. §119(e). Each of the afore-mentioned applications is incorporated herein by reference in its entirety.

FIELD OF THE INVENTION

This invention generally relates to a method and system for reporting medical test results over a network, and more specifically, to providing a registry at which subscribers' medical test results can be accessed over a public network by the subscribers.

BACKGROUND OF THE INVENTION

The potential for contracting life threatening or currently incurable diseases such as human immunodeficiency virus (HIV or acquired immunodeficiency syndrome (AIDS) through sexual contact with infected partners has substantially changed attitudes about engaging in casual sex in our society. While certain measures Carl minimize the risk that a sexually transmissible disease will be transmitted from one partner to another, many people have viewed that risk as too great to justify a sexual relationship with another person. One way in which prospective sexual partners can minimize the risk and alleviate the dampening effects of concern about contracting such diseases from the other partner is to first ensure that each partner has recently been tested for at least life threatening or currently incurable sexual diseases, with negative results.

In many cases, a verbal assurance by a prospective sexual partner that the person has recently been tested for diseases such as HIV, genital herpes, hepatitis B, or hepatitis C will not be sufficient to convince the other partner to engage in sex, since the person giving the assurance may not have been tested or may have been tested with positive results for such diseases. Proof of the testing is somewhat hard to provide, particularly when the prospective sexual union has occurred following a casual meeting or under circumstances in which proof, such as documentation of the medical test results, is not readily available. Clearly, a readily accessible registry that shows proof of recent negative test results for sexually transmitted diseases (STDs) for each partner would greatly reduce the risk of contracting such diseases from a sexual liaison, and the assurance provided by enabling the other prospective partner to access this proof would certainly reduce the concerns of both prospective partners for incurring such risks.

The Internet has become a freely and widely accessible site for all types of information and would provide an ideal medium to enable medical test results to be readily accessed by a party who has been tested and has authorized the test results to be recorded in an accessible registry. The registry in which such test results are stored could be accessed through any computer or other computing device that is coupled to the Internet, from virtually any place in the world. Alternatively, the registry could be accessed by telephone. The only other requirements for such a registry to serve the intended function would be that the access to an individual's test results be securely limited only to the person who was tested and to others provided access by that person, and that the party who was tested be unable to modify the test results that are posted, other than to delete the results. Clearly, it is very important that the other prospective sexual partner be able to rely upon the results of such medical tests to the extent that the tests were properly carried out by a certified testing agency.

The ability to access the results of tests for STDs in an accessible registry would not mean that partners engaging in sex should do so without taking other protective measures, such as using condoms. In fact, it would be desirable to provide education about safe sex practices at the same site as the registry in which the test results are stored and accessed in order to encourage individual awareness of risks, and responsibility and safety in dealing with STDs. The registry site might thus include information of a socially conscious nature or provide links to information concerning the practice of safe sex, in addition to providing the test results for assuring a prospective sexual partner that the other prospective partner was tested and found to be free of STDs, of at least a life threatening or incurable type.

It would also be desirable to employ, a registry accessible over the Internet (or other public network, including the public telephone network) at which test results for other types of medical tests could be stored and accessed by the person tested and/or by authorized medical personnel. While many other types of test results could be accessed on such a site, examples of such tests would be those carried out to measure blood glucose (for diabetes), or to measure protimes (for blood clotting factor), troponin (cardiac function), myoglobin (cardiac function), or creatinine (for renal function). Use of a registry to store these results would minimize paper work and reduce errors in reporting the results.

Also, it would be desirable to store the results of home medical tests at an Internet registry site, so that both the individual being tested and that person's physician are able to access the results. In connection with home testing, it would be preferable to provide an interface between an automated test apparatus designed to carry out the test and the individual's computer to process the test results and transmit them to the registry for storage. For example, the test apparatus might couple to the person's computer through a universal serial bus (USB) port or through a serial or parallel port. Some tests require that a relatively complex analysis be performed to determine the level of a substance in the person's blood or other bodily fluids or in bodily samples (e.g., serum, plasma, urine, saliva, hair, etc.), and such tests are more readily carried out by a personal computer. The results could then be automatically transmitted to the registry site for storage and access by the person's physician or for use in prescribing appropriate drugs, therapy, or prophylactic measures. Alternatively, the test data could be analyzed by the registry site or its affiliated laboratory(ies) and the results made available on the registry site for access by the subscriber or other individual authorized by the subscriber.

Another possible application of this invention is a registry site that is directed to securely storing the results of testing for recreational and illicit drugs (e.g., marijuana, cocaine, opiates, phencylidine, amphetamines, barbiturates, benzodiazepines, methadone, propoxyphene and alcohol). Such a site could be used, for example, by employers and employees or prospective employees where such testing is a requirement of employment, i.e., in law enforcement, judicial and drug rehabilitation settings, or in the required testing of athletes.

Accordingly, it will be apparent that providing a site, which is secure, for storing medical test results accessible over a network (such as the Internet) has many desirable applications. Currently, no such site is available that both provides evidence of the identity of the individual tested and also enables the secure access of test results.

SUMMARY OF THE INVENTION

In accord with the present invention, a method is defined for registering the results of a medical test performed on a subscriber so that the results are accessible only to authorized parties over a communication network and can serve as evidence of a medical condition of the subscriber. The method includes the step of receiving the results of the medical test of the subscriber from a testing agency that performed the medical test, along with an indicia of an identity of the subscriber. Note that for purposes of this specification and of the claims that follow, the terms "testing agency", "testing lab" and "test lab" refer to a facility where blood, other bodily fluid or a bodily sample is collected, together with a facility where the actual testing/analysis is performed. The collection facility and the testing/analysis facility may be located at the same site or at different sites. The results of the medical test of the subscriber are stored at a registry site provided by a subscription service. The subscriber is readily able to access the results of the medical test and the indicia of the identity of the subscriber at the registry site over the communication network to provide evidence to another party of the medical condition of the subscriber, based upon the results of the medical test.

In one preferred application of the present invention, the medical test is preferably a test for a STD, and more preferably, a potentially life-threatening or currently incurable STD. Also, in this preferred application, the other party is likely to be a prospective sexual partner of the subscriber. To ensure the security of the medical test results, the subscriber is preferably provided with an access code including a user name and a password that must be supplied to gain access to the results of the medical test stored at the registry site.

The method also preferably includes the step of requiring the subscriber to authorize transmittal of the results of the medical test from the testing agency to the registry site prior to and as a condition to the step of receiving the results from the testing agency. Once the testing agency is authorized to do so, it electronically transmits the results of the medical test to the registry site.

A history of the results from medical tests performed on the subscriber at different times will also be maintained at the registry site. This testing history will likely include a date at which each medical test was performed, and can be accessed only by authorized parties, e.g., the subscriber.

The subscription service optionally charges the subscriber a fee for providing access by the subscriber to the results of the medical test at the registry site and/or may charge a fee for receiving and storing the results of the medical test.

A link on the registry site can be provided to a different site (maintained by another party) that provides information of potential interest to the subscriber. A fee can then be charged to the other party in regard to the subscriber accessing the different site via the link on the registry site of the subscription service.

It is also contemplated that the registry site provided by the subscription service will display advertising and charge a fee for displaying the advertising.

The subscriber will optionally, be able to access the results of the medical test via an electronic data communication link to the registry site. As used herein and in the claims that follow, the terms "electronic data communication", "communication network" and "communication channel" are intended to encompass all forms of wired and wireless communication, including but not limited to, communication between computing devices, over local and wide area networks, communication using all types of network access devices, telephones, facsimile machines, and all other forms of electrical and electronic communication between disparate sites.

In one embodiment, the subscription service will specify the testing agency that will provide the medical test of the subscriber and will receive a portion of a fee charged to the subscriber by the testing agency for carrying out the medical test. Optionally, the testing agency will provide a discount to the subscriber for using the testing agency that was specified by the subscription service.

The subscriber will be able to delete the entire history of the results of the subscriber's medical tests from the registry site. In addition, the subscriber will be able to determine who will have access to the results of the medical test stored at the registry site. The subscriber can also limit access of a guest to specific parts of the data of the subscriber that are stored at the registry site.

Another aspect of the present invention is directed to a system for enabling limited access to results of a medical test performed on a subscriber so that the results are accessible only to authorized parties over the electronic communication network and can serve as evidence of a medical condition of the subscriber. The system includes a server that stores the results of the medical test and makes the results available to the authorized parties in a manner generally consistent with the steps of the method described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
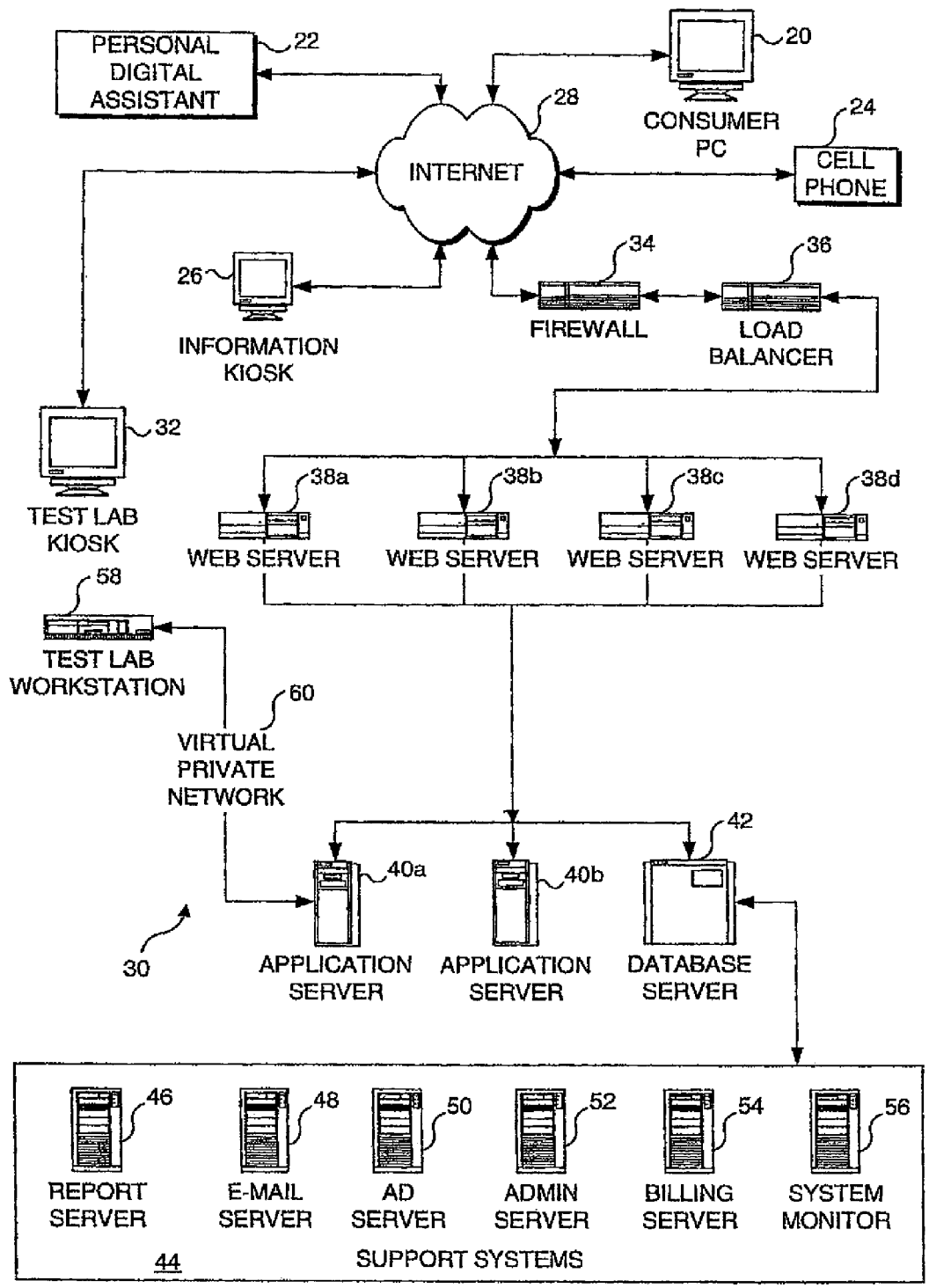
FIG. 1 is a schematic diagram of the components of the present invention.

The present invention makes use of an Internet web site that will serve as a clearing house or registry for STD test results.

Registration of a domain name for such a site has already been secured, and is InformedPartner.com. This web site will provide subscribers secure access to personal information of a very sensitive nature, and will therefore implement extremely high standards of security to ensure that the information is not accessible by unauthorized parties and is not changed to alter the results of a medical test performed on a subscriber. Because the service is only available to subscribers who have registered with the web site, the following discussion and the claims that follow refer to this web site as a "registry site."

Subscribers registering for the service provided by this registry site will have the option of having their STD test results posted to the registry site, along with an independent verification of the subscriber's identity, which is referred to in the claims that follow as "an indicia of the identity of the subscriber." In addition, the subscriber can also post test results that are not associated with verification of the subscriber's identity. In this case, the registry site will simply provide a repository for such data, creating a historical database of medical test results that may be of benefit to the subscriber, and will indicate, in connection with such data, that the identity of the individual tested has NOT been verified. However, the primary purpose of the service provided to the subscriber by the registry site is to enable proof of a medical condition to be presented to a prospective sexual partner of the subscriber based upon the results of one or more medical tests that were performed on the subscriber by a testing laboratory affiliated with the registry site. The subscriber's personal information is securely accessible only by authorized parties via an Internet or other electronic communication connection. Results of a medical test and other personal data of the subscriber can be accessed and displayed to the subscriber or to any other party who has previously been authorized by the subscriber to have access to data of the subscriber by entering a correct user name (and/or a customer ID number (ID) assigned to the subscriber) and the correct password. The subscriber will choose or be assigned a unique password, and will choose or be assigned a unique guest password and/or guest ID number for each specific other party authorized by the subscriber to access a selected portion of the subscriber's personal data. Thus, the subscriber can set access rights that limit the specific data of the subscriber that can be accessed by another party, based upon the password and/or guest ID number entered by the other party, which the subscriber will provide to the other party. A guest permission may optionally be valid for a single use only. Once a guest uses the credentials (the guest ID number and/or guest password) to access the subscriber's data, those credentials will expire, making it impossible for that guest or anyone else not so authorized to access the information on the web site.

Data maintained by the registry site will include personal identification information for each subscriber, a record of the types of medical tests performed on the subscriber, a test date, and test results, all of which will be associated with the customer ID originally assigned to the consumer. This information will be delivered in a format that is appropriate for display on a variety of different types of Internet or electronic communication access instruments.

In FIG. 1, a system diagram illustrates various components of a preferred system for implementing the present invention, including maintenance of data at the registry site, and providing access of that data by a subscriber (or by another party authorized by the subscriber). Currently, it is likely that, in most cases, a subscriber will connect to the registry site using a personal computer (PC) 20 on which a browser program is executed. Examples of suitable browsing programs for execution on PC 20 include Microsoft Corporation's INTERNET EXPLORER™, and Netscape Corporation's NAVIGATOR™ browser programs. However, it is also contemplated that other devices, such as a personal digital assistant (PDA) 22 or a cell phone 24 that are Internet access enabled, can alternatively be used to access medical test results and other personal information of a subscriber that are maintained at the registry site. An appropriate format for the data maintained at the registry site will be provided for the specific Internet or electronic communication device employed to access the data. Thus, PC 20 can access data displayed using the full browser graphic user interface, while only a textual representation of the data will be displayed on cell phone 24. Details such as the type of Internet access employed by a subscriber, e.g., access over conventional telephone lines using, a modem, a cable modem, a high-speed digital subscriber line, or satellite access of Internet 28 are not illustrated in FIG. 1, since these details are not pertinent to the present invention. However, as is evidenced by the inclusion of PDA 22 and cell phone 24, it is contemplated that various types of wired and wireless connections with Internet 28 can be used for electronic data communication with the registry site at which the test results of a subscriber are maintained, A consumer wishing to subscribe to the service, provided by a registry site 30 can initially contact the registry site (to register as a subscriber to the service) over Internet 28 using PC 20, PDA 22, or cell phone 24, or may call the registry site by telephone, or by mail, email, or facsimile transmission. Alternatively, a consumer wishing to subscribe to the service may first become aware of it when exposed to advertising associated with an information kiosk 26 or when the consumer visits a testing lab to be tested for a STD. Each of the testing labs affiliated with the registry site will include one or more testing lab kiosks 32 that are connected to the registry site over Internet 28. It is contemplated that information kiosks 26 will be provided in places such as singles bars, which consumers having an interest in becoming a subscriber to the service provided by the registry site are likely to frequent and in which they are likely to meet prospective sexual partners. The information kiosk or testing lab kiosk can thus provide a connection to the registry site enabling a consumer to become a subscriber of the service. Alternatively, these kiosks can be used to connect to the registry site for access of the test results of a subscriber. Thus, in singles bars and other locations where people may meet others with whom they would be interested in having a sexual liaison, the information kiosks can be employed to provide evidence of a subscriber's medical condition, thereby enabling the subscriber to provide proof that when last tested for a STD, the results of the test were as asserted by the subscriber. Clearly, in most instances, both prospective sexual partners will preferably be subscribers, so that each can provide the proof of the Medical condition that the other prospective partner would prefer.

Revenue Model for Registry Site

As illustrated in FIG. 1, Internet 28 is the most likely channel for a subscriber (or a consumer who wants to register as a subscriber) to access registry site 30. Before making use of the services provided by registry site 30, a consumer must register and thereby become a subscriber; and details of the registration process are discussed below. It is contemplated that a monthly or annual subscription fee, will be charged to a subscriber for providing the services explained herein. In addition to paying a periodic subscription fee, each subscriber will likely be charged each time that test results of medical tests performed on the subscriber are transferred to the registry site for storage, and a smaller charge may be incurred each time that the subscriber's personal data and test results are accessed over Internet 28. It is also contemplated that the registry site will display links to other web sites that provide information of possible interest to subscribers. For example, a link might be provided to a web site that sells birth control-related products, or a link might be provided to a site that discusses newly developed treatments for STDs. The registry site may impose a charge to the other web site each time that the link to the other web site is activated, or may charge a fixed fee for simply including the link. In addition, the registry site will HWY display banner ads and other advertising components for web sites run by others. Typical fees for displaying such advertising at the registry site will be charged to those who are advertising in this manner.

Another source of revenue for the registry site will derive from the registry she specifying the testing labs that are affiliated with the registry site. A portion of the medical test fee charged by such a testing lab will then be received by the operators of the registry site. Since the service of the registry site is at least national, and more likely, will become international, the testing labs required to service all of the subscribers of the registry site will be distributed all over the country, and possibly, in all major countries of the world. Optionally, the testing labs may provide a discount to subscribers of the registry site, recognizing that the increased volume arising from the referral provided by the registry site will more than compensate the testing lab for the portion of the fee returned to the registry site and any discount provided the subscribers of the registry site.

Secure Access of Subscriber Data

A key aspect of the service provided by registry site 30 is the security with which the personal information of each subscriber is maintained. The security of this personal information and the test result data is protected by requiring that each subscriber enter a user name and unique password before being allowed access to the data of the subscriber. In addition, each subscriber is provided with, or can specify, a guest or partner ID number and/or password that must be entered to enable the guest to gain access to that portion of the subscriber's personal information and test results to which the subscriber has authorized access. The subscriber controls the access to this data and information by setting permissions for each specific unique guest or partner ID number. Such permissions will enable the subscriber to determine the information displayed to the guest and the protection level provided. For example, the subscriber can specify whether: (1) the guest requires a guest ID number and a secondary password; (2) the guest is permitted to view only a particular type of test (e.g., a test for STD, but not for drugs); and, (3) the guest ID number and/or password is valid for only a single use or for multiple accesses of the subscriber's information and test results. The guest ID numbers are not sequential, but instead are randomly generated to prevent someone from "guessing" a more current guest ID, based on a previous guest ID.

The web site may optionally include a Digital Certification, providing a verifiable form of identification that the web site being accessed is, in fact, the true registry site, or the web site can provide other means to prove its authenticity as the registry site. For example, the registry site may enable a prospective partner, who also is a subscriber of the registry site, to access his or her test data, using his or her customer ID and/or password, directly from the subscriber's displayed information, to mitigate the risk that inaccurate or fraudulent test results posted on a fraudulent site can be displayed to an unwitting prospective partner. To mitigate the possibility of a third party accessing a subscriber's displayed test results without the permission of the subscriber, the browser may be set to refresh after a short period of time and then automatically display a non-confidential page within the registry site (e.g., a guest login page). All web-based communications accessing personal information and data of a subscriber that are maintained on registry site 30 will be via a secure socket layer (SSL) encrypted Internet connection to registry site 30 and will be through a firewall 34. Firewall 34 isolates the sensitive information of the subscribers, preventing unauthorized access by third parties. Communications through firewall 34 from Internet 28 are connected to a load balancer 36, which distributes the Internet traffic generally equally between a plurality of web servers 38a through 38d, thereby minimizing delays by subscribers and authorized guests in accessing the personal information and test result data. Firewall 34 also restricts access to the web services of each of these web servers and ensures that no outside traffic can directly reach the web servers.

Application servers 40a and 40b form a middle tier in the architecture of registry site 30 and are isolated from the Internet by both firewall 34 and load balancer 36. Only an application running on the application servers can enable access by authorized parties to data of the subscribers maintained on a database server 42. The business logic for the web based application that enables subscribers to access their individual test results and other personal information are hosted by the application servers. Also, the application servers generate dynamic content based on data extracted from the database maintained on database server 42. Any incoming queries from web servers 38a through 38d are dispatched to the application servers, which perform appropriate queries of the data, extracting the requested information once all requirements for secure access have been met. Also, the application servers format the returned data in a form appropriate for the client Internet access device that has queried registry site 30, so that the form is appropriate and can readily be rendered on the PC, PDA, cell phone, or other Internet or electronic access device being used by the subscriber. The output produced from a query of database server 42 will be returned to the web server that requested it, under the control of the application running on one of the application servers.

Another key aspect in maintaining the integrity and security of test result data will be the use of a virtual private network (VPN) 60, which is connected to each affiliated testing lab work station 58. Several different approaches are contemplated for entry of test results into database server 42. One preferred approach is to completely automate the process of reading the test results from medical tests performed on subscribers and to automatically batch load the test results into the data at registry site 30 over VPN 60, so that no human intervention is required for transcribing the test results. Automating this process should minimize the risks of inadvertently introducing an error in the results reported and stored for any subscriber. Alternatively, test results from medical tests of subscribers can be entered in an appropriate form at testing lab work station 58, by trained personnel at the testing lab. It is highly preferred that no personnel at registry site 30 be involved in the processing of test results or entry of the test results into the data maintained on database server 42. By limiting, human interaction in the process only to personnel at the testing lab, any liability of the registry site for error in the result or in the performance of the medical test, or in the entry of the test results into the data will be avoided by the registry site. Transmission of the test results over VPN 60 in an encrypted form (either as an automated batch load or as manual transcription entries on a form) will ensure that the results cannot be intercepted by a third party. Also, since application servers 40a and 40b interact with testing lab work station 58 for providing entry and transmission of the test results into the database maintained on database server 42, they will provide an automated verification of the receipt of the test results by the registry site to the testing lab that submitted the test results.

Strict administrative controls will be enforced on the security of the application and application servers hosting the application that enable access to the subscriber data. All subscriber data contained within database server 42 of a sensitive nature will be encrypted and only accessible by administrator level personnel at the registry site, who because of the encrypted form of the data, will be unable to directly display and read sensitive information of the subscribers contained in the data.

Additional support systems 44 will likely be provided to facilitate the management and administration of registry site 30. Examples of these support systems include a report server 46, an email server 48, an advertising server 50, an administration server 52, a billing server 54, and a system monitor 56. Other support systems will be provided as necessary to administer and manage the operation of the business of the registry site relating to servicing the needs of subscribers and controlling access to the sensitive data maintained on database server 42.

When the lab has posted the test results for a subscriber to the registry site for inclusion in the data maintained there, the subscriber can be notified either by email, by facsimile transmission, or by a phone call (made by the system in an automated fashion) to inform the subscriber that the test results have been uploaded automatically or manually to the registry site and can be accessed by the subscriber. These test results can then be checked by the subscriber. Preferably, the subscriber will not be able to selectively withhold the display of test results from a similar group of test results once said test results have been transmitted to the registry without terminating his or her subscription to the registry, thereby expunging the subscriber's testing data history and invalidating further use of the subscriber's primary username and password. In the event that the subscriber arranges for test results for drug use and test results for STDs to be stored at the registry site, it is contemplated that the subscriber will be enabled to select the type of test results (i.e., drug use test results or STD test results, in this example) to be included among the data that a guest or prospective partner of the subscriber can access to verify the medical condition of the subscriber based upon the results of the lab tests. It is contemplated that automatic notifications of the subscriber by email or facsimile transmission, informing the subscriber that the test results are available on the registry site, can be customized by a particular testing lab to comply with specific trademark branding needs of the testing lab, but will not contain any personal information or the actual test results, as such messages will be transmitted through unsecured channels and might be accessed by third parties. When the registry site receives the test results from the testing lab, an automated verification email message will be transmitted to the testing lab from the registry site, providing proof that the registry site has received those results from the testing lab. Alternatively, the registry site may generate automatic notification of the subscriber that test results are available for review on the registry site.

As an alternative to automated uploading of test results to the registry site, subscribers may elect to have the test results forwarded to them from the testing lab in a more traditional fashion, i.e., by personal mail, or over the telephone. Once the subscriber has received and reviewed the test results, the subscriber can at that time, request that the testing lab post the results to the registry site. Only after receiving permission from the subscriber would the testing lab forward the results of the tests, along with validated identification information for the subscriber, to serve as proof of the subscriber's identity when the test results are accessed at the registry site, by a guest or prospective partner.

It is also contemplated that the subscriber may choose to use one or more kits to carry out medical tasting at home, or may elect to have medical tests performed by a non-affiliated testing lab. Also, some home test kits must be mailed into a testing lab for determination of the results of the tests, A subscriber will have the option of manually posting such tests to the registry site. However, test results that are manually posted and not provided by an affiliated testing lab which has not drawn the test sample from a subscriber whose identity has been verified will not have the benefit of a validation of the subscriber's identity, and thus will be unable to serve as proof of the subscriber's medical condition. Any guest or prospective sexual partner accessing results that are posted without benefit of the validation of the subscriber's identity will be clearly warned in the display of the results that the registry site is posting the results as a service to the subscriber, but without proof of the subscriber's identity. The guest will thus be alerted that the test results do not serve as evidence of the subscriber's medical condition, since They might be fictitious, or may be for a person other than the actual subscriber.

One of the benefits of enabling the subscriber to post medical test results from sources other than an affiliated testing lab and without a proof of identity is to maintain a history of the tests that can be readily accessed by the subscriber. In addition, posting of such test results may be beneficial in facilitating discussions between the subscriber and the subscriber's physician, since it is possible that both the subscriber and the physician can simultaneously access the test results (assuming that the subscriber has provided permission and a guest password and/or guest ID number to the physician to access the results).

Summary of Procedures Used in Present Invention

Figure 2:
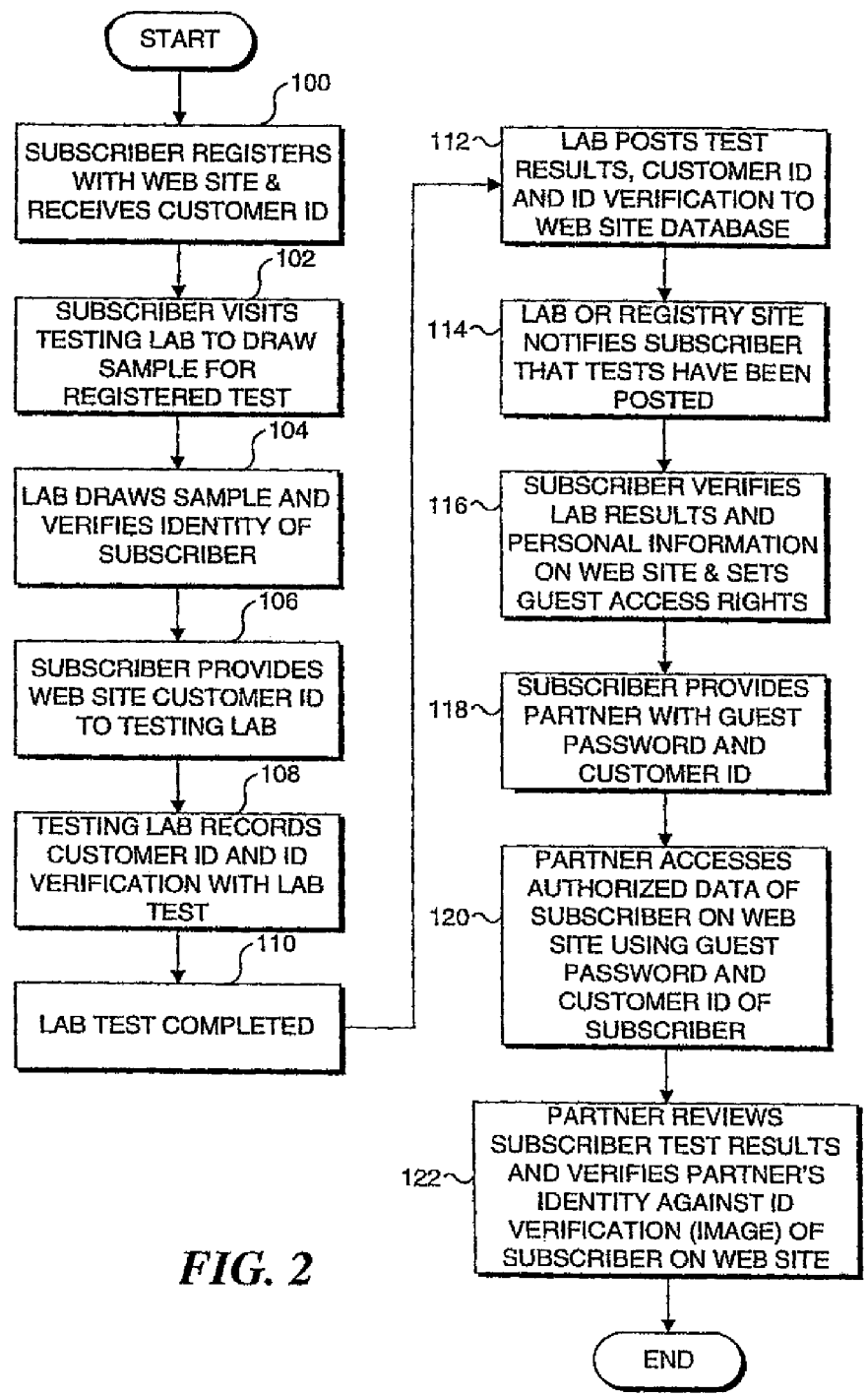
FIG. 2 is an overview flow chart showing the steps implemented in the present invention.

FIG. 2 illustrates the steps involved in the overall use of the registry site for registering subscribers and for receiving, posting, and enabling access of test results that serve as proof of a medical condition of the subscriber. Following a start block, a block 100 indicates that a consumer registers as a subscriber with the registry site (e.g., InformedPartner.com). As part of the registration process, the subscriber may optionally be required to provide an indicia of identification (e.g., a digital copy of a passport photograph or a valid driver's license), although, it will be more likely that the indicia of identification will be required simply to confirm the identity of the subscriber for purposes of payment by a credit or debit card, or by other non-cash means. As noted above, the registration can be accomplished over a variety of different types of devices that can access the registry site over the Internet, including information kiosk 26, and testing lab kiosk 32. By registering with the registry site, the subscriber agrees to be financially liable for the subscription fee and for any other fees associated with the subscriber's use of the registry site. As noted above, such fees may include a fee charged each time that the personal information and data of the subscriber are accessed, and a fee charged each time that medical test results are posted to the registry site. In a block 102, the subscriber visits an affiliated testing lab, having arranged for the testing lab to draw a sample in order to carry out the test requested by the subscriber. It is possible that the appointment for visiting the testing lab will be made from the registry site, but can alternatively be made over the telephone or during a previous visit to the testing lab. For the purposes of this exemplary application of this invention, the medical tests will likely be for STDs, and more likely, be limited to potentially life threatening or currently incurable kinds of STDs.

Examples of the types of tests that might be made for potentially life-threatening or currently incurable STDs include the Elisa immunoassay (EIA), the Western blot or other confirmatory test for HIV; the hepatitis 13 surface antigen and hepatitis C antibody tests; and the Herpes simplex virus type 2 (HSV 2)-specific serology test. Additional tests for curable sexually, transmissible diseases may be included, such as culture, ligase chain reaction (LCR) and polymerase chain reaction (PCR) tests for chlamydia trachomatis and neisseria gonorrhoeae; rapid plasma reagin (RPR), Venereal Disease Research Laboratories (VDRL) or other confirmatory test for syphilis; and tests for Epstein-Barr virus (EBV), cytomegalovirus (CMV) and varicella-zoster virus (VZV). Of course, many other types of tests may be carried out within the scope of the present invention, including those for other types of medical conditions that are not sexually transmitted and/or are tests for diseases or medical conditions that are not incurable or potentially life threatening.

In a block 104, the lab draws a sample from the subscriber and at that time, verifies the identity of the subscriber. Verification of the identity of the subscriber can be based upon presentation by the subscriber of any kind of legally acceptable picture identification, such as a driver's license, passport, or other common legally accepted indicia of identification. However, in most cases, it is expected that a subscriber will present a driver's license with a picture as proof of his or her identity. The testing lab also may access (e.g., only at an access level necessary for interaction with medical testing lab providers) the subscriber's identification information on the registry site to match the presented indicia of identification to that on the registry site, if such identification information was provided previously by the subscriber to the registry site. A block 106 indicates that the subscriber provides to the testing lab the customer ID that was obtained from the registry site, so that the customer ID can be associated with the test results and with the subscriber identification data. Optionally, such customer ED can be verified by the testing lab by accessing the registry site. Although various types of identification data are contemplated, the simplest verification data for the subscriber's identification is the driver's license number of the subscriber.

In a block 108, the testing lab records the customer ID and the ID verification in association with the lab test, on the request form. In a block 110, the lab completes the medical tests requested by the subscriber, obtaining results that are then posted (automatically or manually) to the registry site, along with the customer ID and identification verification data, as indicated in a block 112. As noted above, it is also contemplated that the subscriber may alternatively choose to receive and verify the test results before requesting that the testing lab post them to the registry site.

A block 114 indicates that the testing lab or registry site notifies the subscriber that the test results have been posted to the registry site. The notification can be automated, as described above. The subscriber verifies the lab results and the personal information on the registry site, typically using a browser to access the information. Of course, the results of the test can only be accessed by the subscriber after the subscriber enters the user name and password previously assigned to the subscriber. In addition, a block 116 provides for the subscriber to set the guest access rights, specifically defining the data of the subscriber that will be accessible to a guest or prospective sexual partner. Preferably, the subscriber will be unable to deny a guest or prospective partner access to selected test results contained in the subscriber's testing history, other than by type of test results, as noted above. Thus, for example, a subscriber will not be allowed to authorize access to only a portion of STD test results for the subscriber, but will be allowed to authorize access by a guest to only all of the subscriber's STD test results, while excluding access by the guest to the subscriber's drug use test results, or vice versa.

Typically at some later point in time, the subscriber will interact with a potential sexual partner. In order to show proof of a medical condition satisfying the prospective sexual partner, the subscriber will provide the prospective partner with the guest password/and or guest ID number and customer ID for the subscriber as indicated in a block 118, As noted in a block 120, the prospective sexual partner can then access the authorized data of the subscriber on the registry site using the guest password and/or guest ID number, and customer ID) of the subscriber. A block 122 indicates that the guest or prospective partner reviews the subscriber's test results and verifies the person's (subscriber's) identity against the identification verification data included with the test result data of the subscriber on the registry site. Assuming that the identification verification data confirm that the identity of the subscriber who was tested is that of the person asserting a medical condition, the prospective partner will at least be assured that, at the time of the medical test, the results shown at the registry site were valid. Naturally, such test results may no longer be applicable. The longer the time interval between the current date and the date of the medical tests, the less assured a prospective partner will be by viewing the test results of a subscriber. For this reason, it is likely that subscribers will be tested more frequently than, they would otherwise, which should help (statistically) in detecting any STD-infected subscribers at an earlier time than would otherwise be the ease. Also, the registry site will provide educational content directed to STDs, including epidemiology, clinical manifestations, diagnosis, treatment, and references to or copies of the most recent scientific literature, relating- to topics of potential interest to the subscriber, and will make very clear that subscribers and guests are encouraged to practice safe sexual procedures to minimize the risk of infection front any type of STD.

An alternative embodiment of the present invention is directed to a registry site that is intended to be accessed telephonically. The subscriber would access the registry site via a telephone access number and enter his or her customer ID and password through an alpha-numeric keypad. The subscriber also could provide a guest or prospective partner with the subscriber's customer ID and a guest password and/or ID number that, through similar use of an alpha-numeric keypad, would allow access to the subscriber's information on the registry. The guest or prospective partner then would be allowed to hear an automated listing of the subscriber's testing history. The automated response would include the subscriber's driver's license number or other identifying information that could be matched against the corresponding information presented by and identifying the party claiming to be the subscriber. If the two parties are located together when the registry is accessed telephonically and the guest or prospective partner also is a subscriber (i.e., a "partner subscriber") to the registry site, the partner subscriber, without terminating the call and redialing, would enter his or her customer ID and password, thereby accessing the partner subscriber's testing history and verifying that the automated response previously heard was, indeed, generated by the registry site and was not a fraudulent automated recording from some other source. The partner subscriber then could allow the subscriber to hear the automated listing of the partner subscriber's testing history and identifying information.

Details of Registering as a Subscriber

Figures 3, 4, 5:
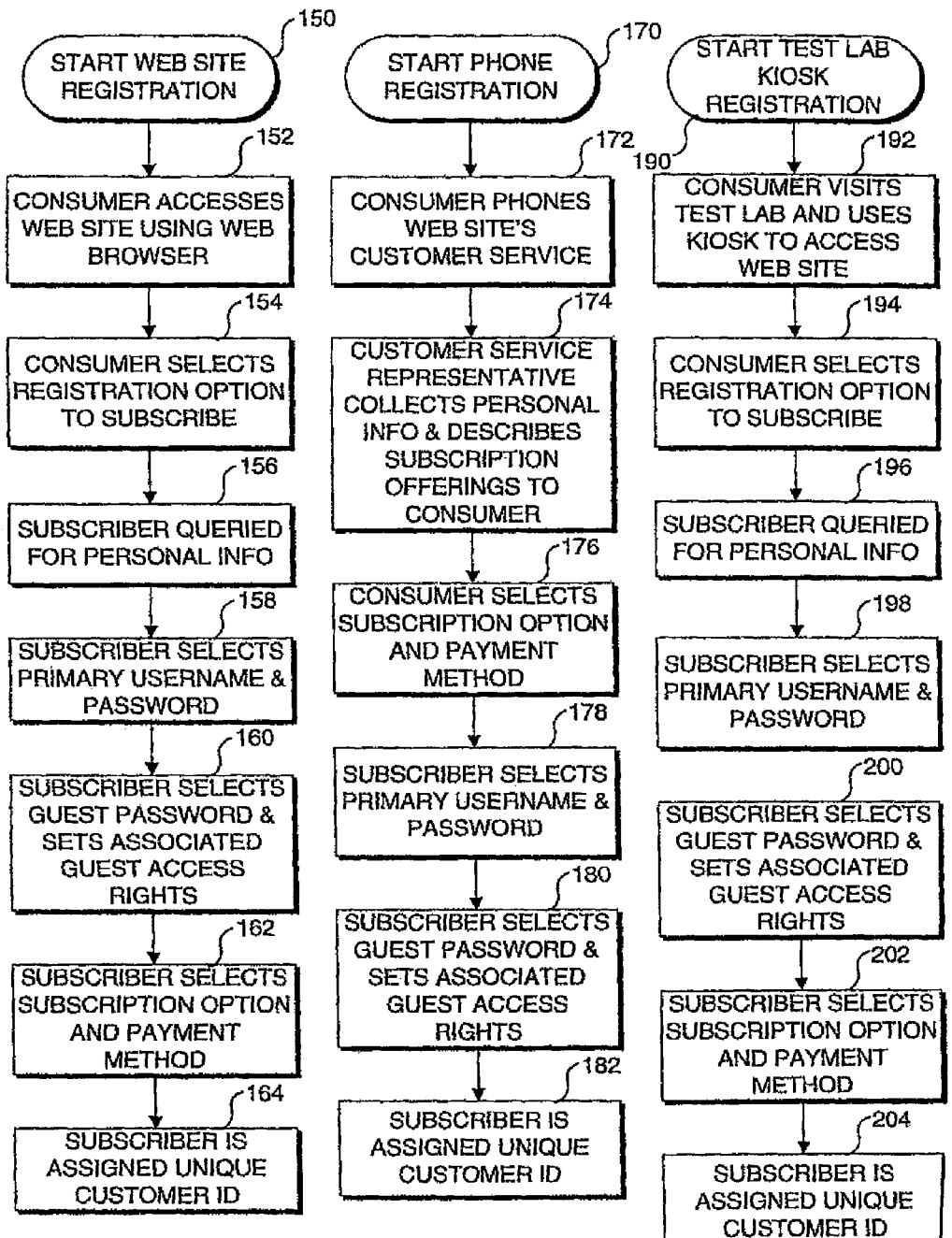
FIG. 3 is a flow chart showing the steps implemented in an online registration of a subscriber in the present invention.
FIG. 4 is a flow chart showing the steps implemented in a mail or phone registration of a subscriber in the present invention.
FIG. 5 is a flow chart showing the steps implemented when a subscriber registers at a kiosk.

Further details of the steps taken by a consumer to register with the registry site as a subscriber are illustrated in FIGS. 3 through 5. These Figures illustrate three different approaches that can be used. FIG. 3 shows the steps involved in registering with the registry site over the Internet, beginning with a block 150. In a block 152, a consumer who is considering becoming a subscriber to the service offered by the registry site accesses the site using a web browser. In a block 154, the consumer selects a registration option provided on a web page of the registry site in order to subscribe to the service. Having selected this option, a block 156 indicates that the subscriber is queried to provide personal information, e.g., by displaying a registration form in the consumer's browser. Such information may include birth date, gender, mailing address, phone number, email address, etc. The subscriber then selects a primary user name and password, as indicated in a block 158. In addition, as noted in a block 160, the subscriber selects a guest password and/or guest ID number and sets the associated guest access rights. In many cases, the subscriber may not choose to disclose all test results to a guest, but may limit the data accessible to the guest to the results of a most recent test for STDs. Preferably, the subscriber will be unable to deny a guest or prospective partner access to selected test results from the subscriber's testing history for a particular type of test, e.g., access to only a portion of the STD test results.

A block 162 provides that the subscriber selects the subscription option and provides a payment method, which will typically be a credit card. The information typically required for accepting payment by credit card will be provided by the subscriber at this time, including the type of credit card, card number, expiration date of the card, billing address, etc. It is also contemplated that other forms of payment can be provided, including payment by debit card, and by other financial instruments, including personal check. Once this information has been entered at the registry site over a SSL connection, a block 164 indicates that the subscriber is assigned a unique customer ID, which is provided to the subscriber for use in referencing the subscriber's personal information and test results on the registry site.

Alternatively, a consumer may elect to register with the registry site over the phone as indicated in a block 170. If so, a block 172 provides that the consumer phones the customer service department for the registry site. In a block 174, a customer service representative answering this telephone call collects the personal information from the consumer and describes the subscription offerings to the consumer, answering any other questions the consumer may have. In a block 176, the consumer selects the subscription option and chooses a payment method, Again, the various conventional ways of providing payment to the registry site for the services rendered will include credit or debit cards and other financial instruments. In a block 178, the subscriber selects a primary user name and password, while in a block 180, the subscriber chooses a guest password and/or guest ID number and sets the associated access rights for a guest. Finally, in a block 182, the subscriber is assigned a unique customer ID number that is given to the customer over the telephone.

FIG. 5 illustrates steps that are similar to those in FIG. 3, except that as indicated in a block 190, the consumer initiates the registration from a testing lab kiosk (or from an information kiosk that might be found in locations likely frequented by those interested in the services provided by the registry site). A block 192 provides that, in this case, the consumer visits the testing lab, perhaps already having arranged for a test to be made for one or more STDs without knowledge of or direction from the registry site. While making the visit, the consumer may learn that the services offered by the registry site are available and will then use the kiosk to access the registry site. In a block 194, the consumer again selects the registration option provided on the homepage of the registry site in order to subscribe to the services offered. Remaining blocks 196 through 204, respectively, in FIG. 5, correspond to blocks 156 through 164 in FIG. 3.

Verification of Subscriber Identification

Figures 6, 7:
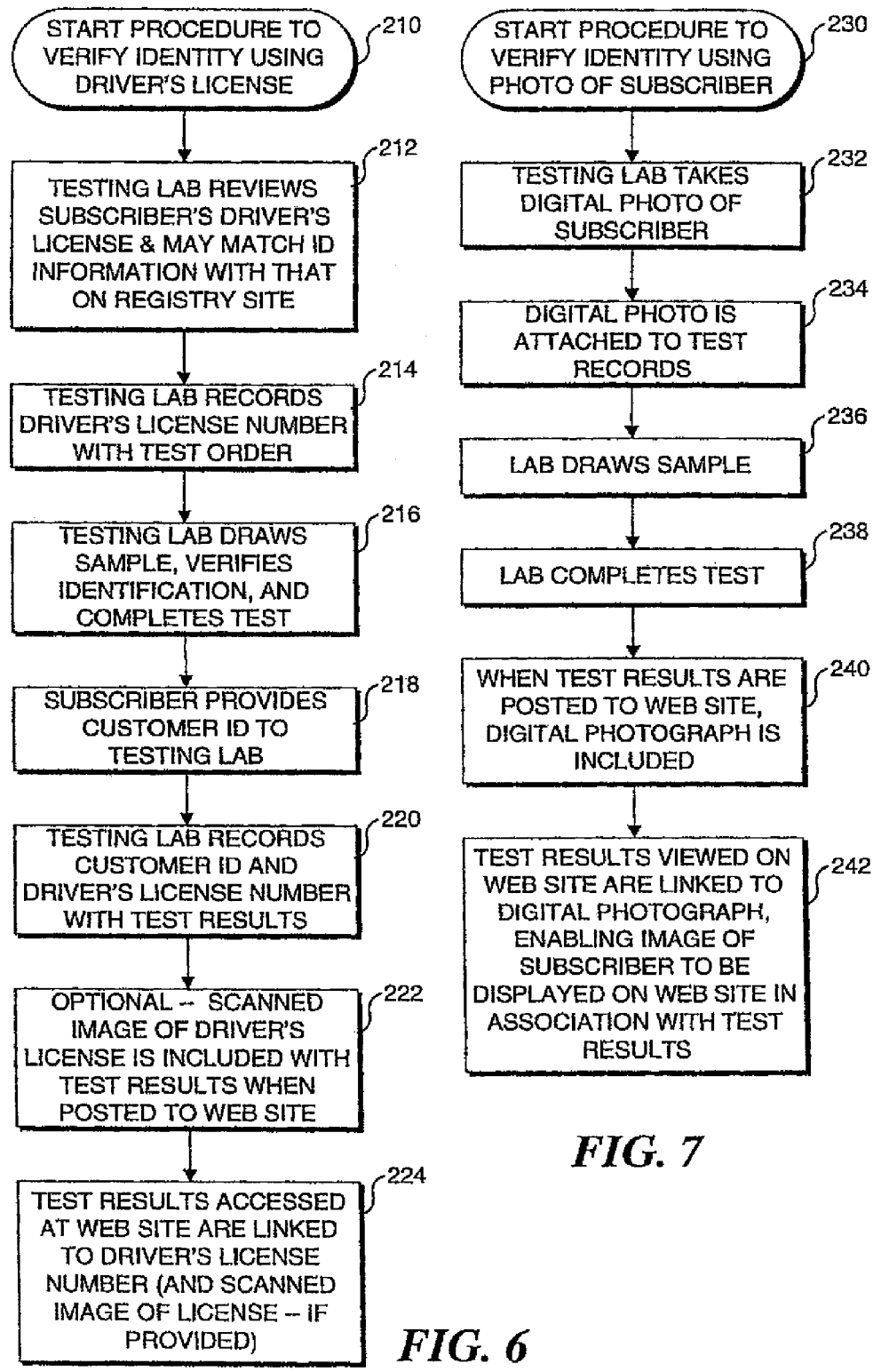
FIG. 6 is a flow chart showing the steps for verifying identity of the subscriber with a driver's license.
FIG. 7 is a flow chart showing the steps involved in taking a digital photograph of a subscriber to prove identity.

FIGS. 6 and 7 illustrate two alternative methods for verifying the subscriber's identification-both at the time the subscriber appears at the testing lab to "be tested," and later, when the test results are accessed by a guest or prospective sexual partner on the registry site. In regard to FIG. 6, the procedure begins with a block 210 in which the subscriber's driver's license (or other indicia of identification) is used as a basis for verifying identity. Accordingly, in a block 212 the testing lab reviews the subscriber's driver's license to confirm that the picture shown there corresponds to the appearance of the person from whom the test sample is drawn. In addition, the testing lab may access (but preferably only at an access level necessary for interaction with medical testing providers) the subscriber's identification information on the registry site to confirm that the subscriber's identification matches that of the individual undergoing the test. Based upon a determination that the person appears to be the individual identified by the driver's license (and matches the indicia of identification on the registry site, if accessed), a block 214 indicates that the testing lab records the driver's license number in association with the test ordered by the subscriber for STDs (or other type of test). Preferably, the recorded indicia of identification accompany the test sample electronically throughout the sample's testing process. According to a block 216, the testing lab then draws a sample from the subscriber whose identification has been confirmed, and completes the test using standard testing procedures. In a block 218, as previously noted, the subscriber also provides the customer ID, that was obtained from the registry site when the subscriber registered, to the testing lab for association with the test results, In a block 220, the testing lab records the customer ID and driver's license number for the subscriber with the test results obtained upon completing the test or analysis.

A block 222 provides that an optional further confirmation of the verification of the identification can be provided by scanning the image (photograph) of the subscriber included on the driver's license using a conventional scanner. The scanned image can be posted with the test results to the registry site and viewed by a guest accessing the test results with the permission of the subscriber as further proof confirming the identity of the subscriber in connection with the test results. In a block 224, the test results accessible at the registry site are linked to the driver's license number (and to the scanned image of the driver's license submitted by the subscriber, if available).

An alternative for providing verification of the identification of the subscriber is shown in FIG. 7, beginning with a block 230. In a block 232, the testing lab takes a digital photograph of the subscriber using any of the readily available digital cameras. The digital photograph produced by the camera is attached to the test request by the testing lab in a block 234 and, preferably, accompanies the sample electronically through the sample's testing process. In a block 236, the testing lab draws a sample from the subscriber and completes the tests requested by the subscriber in a block 238. When the test results are posted to the registry site, as indicated in a block 240, the digital photograph is included and is associated with the test results. Thus, as provided in a block 242, the test results can be viewed on the registry site, linked to the digital photograph. Thus, the image of the subscriber is displayed on the registry site in association with the test results as proof of the identity of the subscriber, thereby providing evidence to a guest who has received permission from the subscriber to access the test results and the digital photo, of the medical condition asserted by the subscriber, as confirmed by the test results.

It is also contemplated that other types of identification can be employed as an alternative to the driver's license number, scanned image of the driver's license, and digital photograph of the subscriber. For example, biometric data of the subscriber may be taken at the time a test sample is drawn from the subscriber and included with the test results that are posted at the registry site. Confirmation of the identity of the subscriber can then be achieved by a guest accessing the test results if the party claiming to be the subscriber has already submitted corresponding biometric data to the registry site. The registry site can then indicate whether the biometric data submitted when the subscriber registered with the site matches the biometric data recorded when the subscriber was tested by the testing lab, thereby confirming that the subscriber tested is in fact the party asserting the medical condition confirmed by the test results. In addition, the biometric data to be compared to that accompanying the test results may be submitted in the presence of the guest, thereby further confirming the identity of the subscriber who was tested matches that of the party asserting a medical condition confirmed by the test results. The biometric data may be a retinal scan, digital fingerprint scan; facial scan, voice print, etc. Input devices for scanning any of these various types of biometric data may eventually be more commonly available, making this alternative more practical.

It is contemplated that in some cases, a subscriber will desire medical results to be posted and will permit access by a guest or prospective partner to those test results even though the results confirm that the subscriber has tested positive for a STD. For example, a prospective partner may have refused a sexual liaison with the subscriber because of concern of infecting the subscriber, if the prospective partner has tested positive for HSV-2. In this case, the prospective partner may wish to confirm that the subscriber has also tested positive for HSV-2, thereby alleviating, to some extent, the concerns that either may infect the other.

A subscriber will not be able to change the test results that are posted to the registry site and, preferably, the subscriber will not be able to deny a guest or prospective partner access to selected tests from the subscriber's testing history. However, at any time, the subscriber may delete or purge his or her entire history of medical tests from the registry site's database, terminating his or her subscription with the site and invalidating his or her customer ID number.

Further Details of the Process

Figures 8, 9, 10:
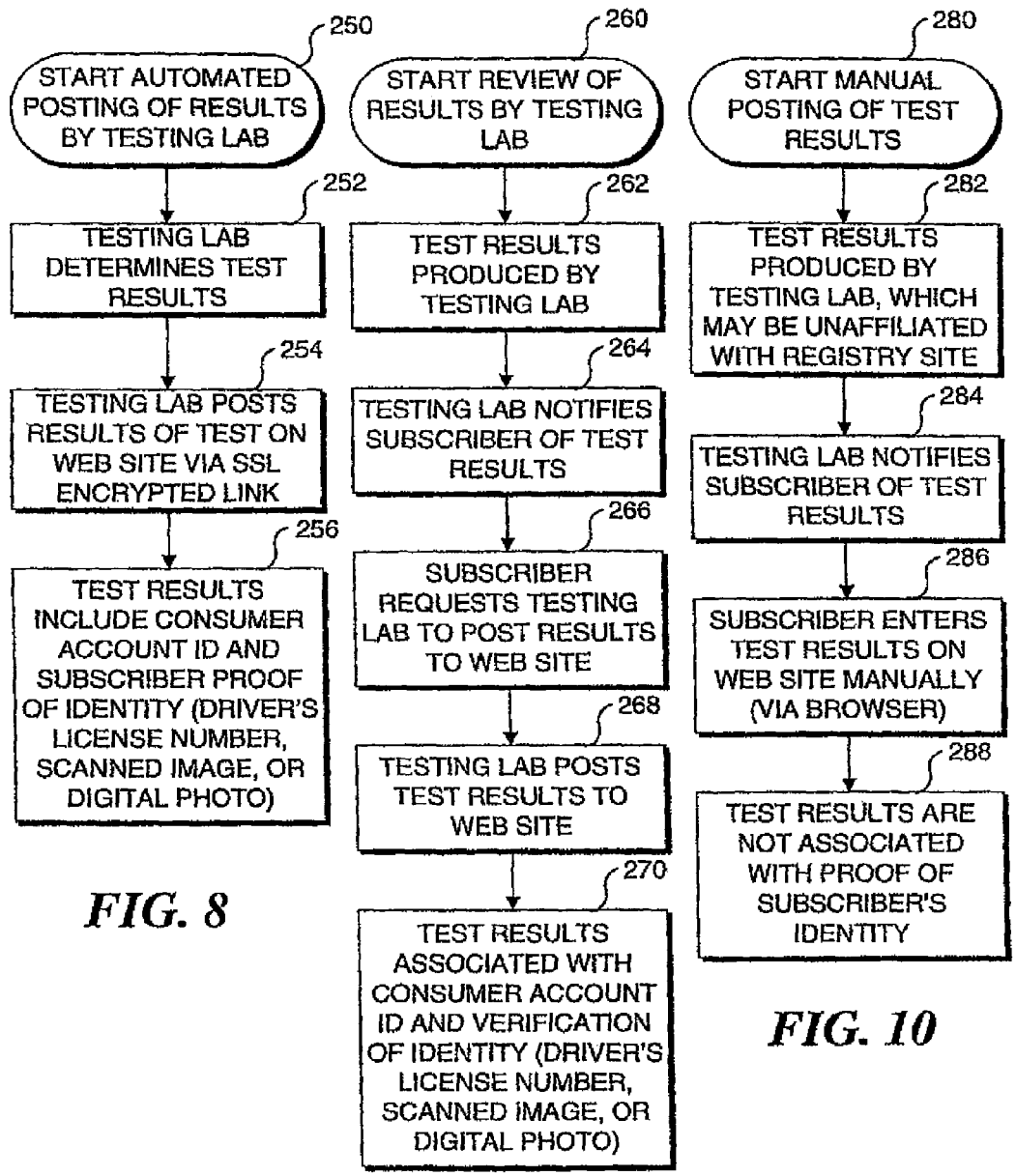
FIG. 8 is a flow chart listing the steps for automatic posting of test results by a laboratory.
FIG. 9 is a flow chart showing the steps involved when a subscriber reviews the test results and then decides to post them on the site.
FIG. 10 is a flow chart showing the steps taken to manually post the test results on the web site.

Further details of the overall process disclosed in FIG. 2 are illustrated in FIG. 8 through 10. For example, FIG. 8 begins with a block 250 in which the steps involved in posting the results of a test in an automated fashion are carried out by the testing lab. A block 252 provides that the test is completed to determine the results. In a block 254, the testing lab posts the results of the test to the registry site via an SSL encrypted link, through a VPN, ensuring that the test results are not intercepted by any third party. If these test results are posted to the registry site without intervention of any personnel at the registry site, the potential for introducing an error in the posting of the results is minimized. Although the registry site cannot attest to the accuracy of the test performed by the testing lab, the process employed for automatically posting the results of the test to the registry site ensures, that further errors are not introduced. As indicated in a block 256, the test results will include the consumer account ID, thereby relating the test results to a specific subscriber, and a proof of the identity of a subscriber, such as the driver's license number, scanned image of the subscriber's driver's license, or a digital photograph of the subscriber.

With reference to FIG. 9, a block 260 begins the alternative process of enabling the subscriber to review the test results before they are posted to the registry site. In a block 262, the test results are produced by the testing lab as requested by the subscriber. A block 264 provides that the testing lab notifies the subscriber of the test results, by telephone, mail, or other relatively secure format. After reviewing the test results, the subscriber has the option of requesting that the testing lab post the results to the registry site, as indicated in a block 266. Assuming that the subscriber has made such a request, block 268 indicates that the testing lab posts the test results to the registry site for access by the subscriber and by any guest given permission by the subscriber. Further, as noted in a block 270, the test results are associated with the consumer account ID provided to the subscriber by the registry site and with the verification of the subscriber's identity, such as the subscriber's driver's license number, the scanned image of the driver's license, or the digital photograph taken of the subscriber.

FIG. 10 illustrates the steps taken for manually posting test results to the registry site, where it is understood that these results do not serve as proof of a medical condition, i.e., for purposes of convincing a prospective sexual partner that the subscriber was tested or that the asserted medical condition was determined by a test of the subscriber. In a block 280, the steps for manually posting the test results begin. A block 282 provides that the test results are produced by a testing lab, but can be based upon a sample submitted by the subscriber after using a home test kit, or as a sample from the subscriber submitted to a testing lab that is not affiliated with the registry site. In a block 284, the testing lab notifies the subscriber of the test results. The subscriber then enters the test results on the registry site manually, for example, by making entries within a browser displayed form provided on the registry site, as indicated in a block 286. However, as noted in a block 288, the test results thus entered are not associated with any proof of the subscriber's identity, and therefore cannot serve as evidence of a medical condition if presented to a guest authorized by the subscriber to view the results.

Figure 11:
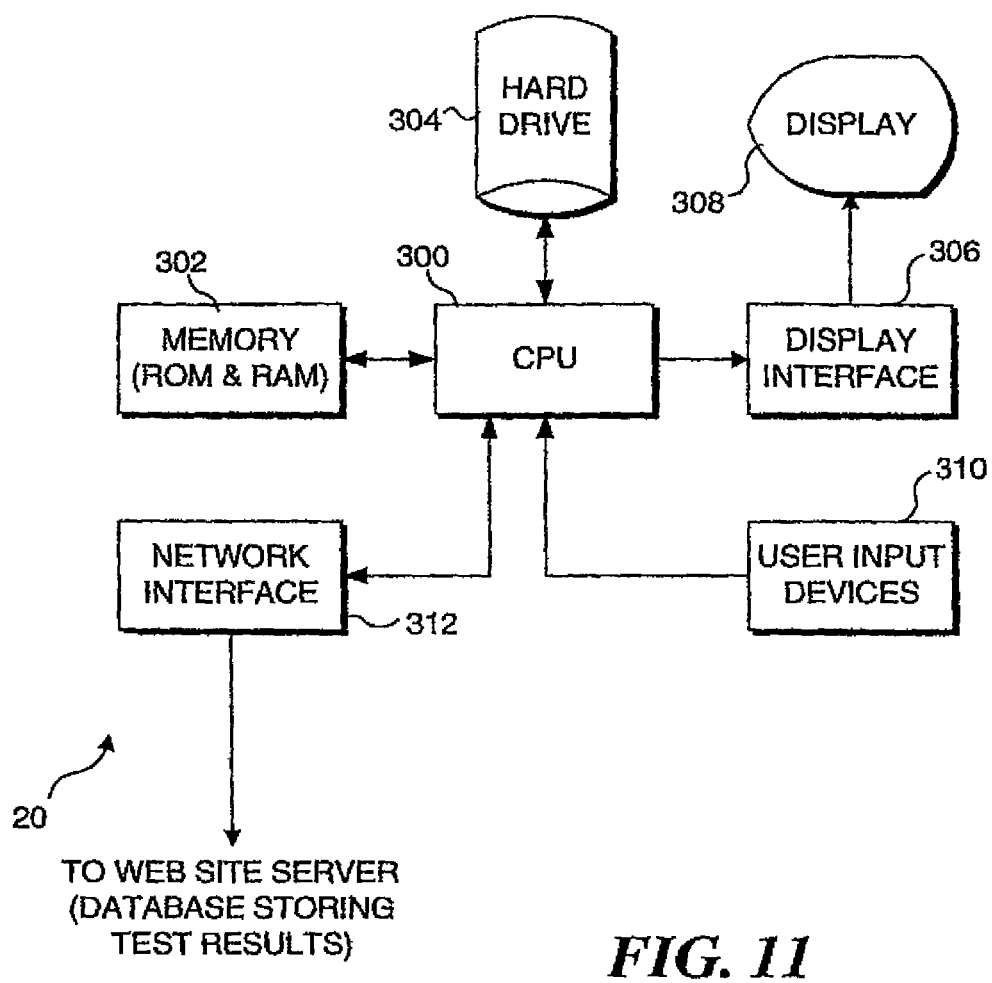
FIG. 11 is a block diagram showing principle functional components of a personal computer suitable for implementing the present invention.

FIG. 11 illustrates basic components of PC 20, which currently is likely to be the most commonly used device for connecting to the registry site over the Internet. These components include a central processing unit (CPU) 300 that is coupled in communication with a memory 302, which includes both read-only memory (ROM) and random access memory (RAM). Memory 302 is loaded with machine instructions that are typically stored on a hard drive 304. The machine instructions, which comprise program modules and other software components of applications such as a browser are executed by CPU 300. Thus, the CPU can execute a browsing program used to access the registry site and to view information of a subscriber, including the test results and verification of the subscriber's identity. CPU 300 is connected to a display interface 306, which drives a display 308, on which the browser displays information obtained by access of the registry site. To connect to the registry site, CPU 300 receives and transmits data bi-directionally over a network interface 312 in response to commands input by the user through user input devices 310, which may include a keyboard and/or pointer control device (or mouse). Network interface 312 may include a modem, or a network interface card that connects to a data communication port on a network through which the registry site is accessed over the Internet, generally as shown in FIG. 1.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A computer-implemented method for registering results of a first medical test on a subscriber so that the results are accessible only to authorized parties over a communication network, as evidence of a medical condition of the subscriber, the computer-implemented method comprising:
    under the control of one or more computing devices,
        receiving, at a registry site from a testing agency that performed the first medical test, the results of the first medical test of the subscriber and an indicator of an identity of the subscriber comprising an image of at least the face of the subscriber, wherein the indicator of the identity of the subscriber is distinct from the results of the first medical test, wherein the indicator is generated by the test agency in conjunction with administration of the first medical test, and wherein the first medical test corresponds to at least one predefined type of medical test, and wherein the at least one predefined type of medical test is not modifiable by the subscriber;
    processing the indicator of the identity of the subscriber with the results of the first medical test to link the indicator of the identity of the subscriber and the results of the first medical test;
    storing, in a data store associated with the registry site, the results of the first medical test of the subscriber together with the indicator of the identity of the subscriber to which the results are linked;
    receiving, from a party authorized by the subscriber, a request for at least the results of the first medical test; and
    providing, to the party authorized by the subscriber, all results of medical tests corresponding to the at least one predefined type of medical test and the linked indicator of the identity of the subscriber that is stored in the data store associated with the registry site.

2. The computer-implemented method of claim 1, wherein the indicator of the identity of the subscriber is verified based at least in part on subscriber information stored at the registry site.

3. The computer-implemented method of claim 2, wherein the indicator of the identity of the subscriber is verified by the test agency.

4. The computer-implemented method of claim 1 further comprising:
    receiving, at the registry site, results of a second medical test of the subscriber, wherein the second medical test corresponds to the at least one predefined type of medical test, and wherein the results of the second medical test of the subscriber are received without an indicator of the identity of the subscriber generated by the test agency in conjunction with administration of the second medical test; and
    storing, at the registry site, the results of the second medical test of the subscriber;
    wherein providing all results of medical tests corresponding to the at least one predefined type of medical test includes providing, to a party authorized by the subscriber, the results of the second medical test of the subscriber in conjunction with the results of the first medical test.

5. The computer-implemented method of claim 4 wherein providing all results of medical tests corresponding to the at least one predefined type of medical test includes causing the display of both the results of the first medical test and the results of the second medical test, wherein display of the results of the first medical test includes display of the indicator of the identity of the subscriber, and wherein display of the results of the second medical test includes display of a visual indicator indicating that: (i) the results of the second medical test of the subscriber are not linked to an indicator of the identity of the subscriber and are not verified; and (ii) an entity that provided a sample used for conducting the second medical test is not confirmed.

6. The computer-implemented method of claim 1 further comprising providing, to the party authorized by the subscriber, registry site verification information, the registry site verification information to be used by the party authorized by the subscriber in verifying the trustworthiness of the registry site.

7. The computer-implemented method of claim 6, wherein the registry site verification information includes a digital certificate.

8. The computer-implemented method of claim 1, wherein the test agency is authorized by the subscriber to provide the results of the first medical test of the subscriber to the registry site.

9. The computer-implemented method of claim 8, wherein the authorization of the test agency by the subscriber to provide the results of the first medical test to the registry site is required as a precondition to the subscriber reviewing the results of the medical test.

10. The computer-implemented method of claim 1, wherein the subscriber is prohibited from denying access to the party authorized by the subscriber to any results of medical tests corresponding to the at least one predefined type of medical test stored in the data store associated with the registry site.

11. The computer-implemented method of claim 1, wherein denying access to any results of medical tests corresponding to the at least one predefined type of medical test stored in the data store associated with the registry site includes at least one of removing results of medical tests from the data store and modifying permissions associated with results of medical tests stored in the data store.

12. The computer-implemented method of claim 1, wherein the subscriber is prohibited from modifying the results of the first medical test at the registry site.

13. A system for managing medical test results of a subscriber so that the results are accessible only to authorized parties over a communication network, as evidence of a medical condition of the subscriber, the system comprising:
    a data store for maintaining results of one or more medical tests of the subscriber, wherein the results of at least one medical test of the subscriber are linked within the data store to an indicator of an identity of the subscriber collected comprising an image of at least the face of the subscriber generated by the test agency that performed the medical test in conjunction with administration of the medical test, wherein the indicator is distinct from the results of the medical test; and a processing unit in communication with the data store, wherein the processing unit is configured to:

receive, from a test agency, the results of a first medical test of the subscriber performed by the test agency and an indicator of an identity of the subscriber comprising an image of at least the face of the subscriber, wherein the indicator is generated by the test agency in conjunction with administration of the first medical test, wherein the first medical test corresponds to at least one predefined type of medical test, and wherein the indicator is distinct from the results of the first medical test;

process the indicator of the identity of the subscriber with the results of the first medical test to link the indicator of the identity of the subscriber and the results of the first medical test;

store, in the data store, the results of the first medical test of the subscriber linked to the indicator of the identity of the subscriber;

receive, from a party authorized by the subscriber, a request for at least the results of the first medical test; and provide, to the party authorized by the subscriber, the results of the first medical test and linked indicator of the identity of the subscriber.

14. The system of claim 13, wherein the processing unit is further configured to:

receive results of a second medical test of the subscriber, wherein the second medical test corresponds to the at least one predefined type of medical test, and wherein the results of the second medical test of the subscriber are received without an indicator of the identity of the subscriber;

store, in the data store, the results of the second medical test of the subscriber; and provide, to the party authorized by the subscriber, access to the results of the second medical test of the subscriber.

15. The system of claim 14, wherein the processing unit is configured to provide the results of the first medical test and provide the results of the second medical test by display of both the results of the first medical test and the results of the second medical test, wherein display of the results of the first medical test includes display of the indicator of the identity of the subscriber, and wherein display of the results of the second medical test includes display of a visual indicator indicating that: (i) the results of the second medical test of the subscriber are not linked to an indicator of the identity of the subscriber and are not verified, and (ii) an entity that provided a sample used for conducting the second medical test is not confirmed.

16. The system of claim 13, wherein the processing unit is further configured to provide, to the party authorized by the subscriber, registry site verification information, the registry site verification information to be used by the party authorized by the subscriber in verifying the trustworthiness of the registry site.

17. The system of claim 16, wherein the registry site verification information includes a digital certificate.

18. The system of claim 13, wherein the test agency is authorized by the subscriber to provide the results of the first medical test of the subscriber to the registry site.

19. The system of claim 18, wherein the authorization of the test agency by the subscriber to provide the results of the first medical test to the registry site is required as a precondition to the subscriber reviewing the results of the first medical test.

20. The system of claim 13, wherein the processing unit is further configured to prohibit the subscriber from denying access to the party authorized by the subscriber to any results of medical tests corresponding to the at least one predefined type of medical test stored in the data store.

21. The system of claim 13, wherein denying access to any results of medical tests stored corresponding to the at least one predefined type of medical test in the data store includes at least one of removing results of medical tests from the data store and modifying permissions associated with results of medical tests stored in the data store.

22. The system of claim 13, wherein indicator of the identity of the subscriber is verified by the test agency that performed the medical test.

23. The system of claim 13, wherein the subscriber is prohibited from modifying the results of the first medical test stored in the data store.

24. A system for registering results of a medical test on a subscriber so that the results are accessible only to authorized parties over a communication network, as evidence of a medical condition of the subscriber, the system comprising:

a data store for maintaining results of one or more medical tests of the subscriber, wherein the results of at least one medical test of the subscriber are linked within the data store to an indicator of an identity of the subscriber comprising an image of at least the face of the subscriber, wherein the indicator is generated by the test agency that performed the medical test in conjunction with administration of the medical test, and wherein the indicator is distinct from the results of the medical test;

a processing unit in communication with the data store, wherein the processing unit is configured to:

receive, from a test agency, results of a first medical test of the subscriber performed by the test agency and an indicator of the identity of the subscriber comprising an image of at least the face of the subscriber, wherein the indicator generated by the test agency in conjunction with administration of the first medical test, wherein the first medical test corresponds to at least one predefined type of medical test, wherein the at least one predefined type of medical test is not modifiable by the subscriber, and wherein the indicator is distinct from the results of the first medical test;

process the indicator of the identity of the subscriber with the results of the first medical test to link the indicator of the identity of the subscriber and the results of the first medical test;

store, in the data store, the results of the first medical test of the subscriber linked to the indicator of the identity of the subscriber;

provide, to a party authorized by the subscriber, registry site verification information, the registry site verification information to be used by the party authorized by the subscriber in verifying trustworthiness of the registry site;

receive, from a party authorized by the subscriber, a request for at least the results of the first medical test; and provide, to the party authorized by the subscriber, the results of the first medical test linked to indicator of the identity of the subscriber.

25. The system of claim 24, wherein the processing unit is further configured to:
- receive results of a second medical test of the subscriber, wherein the results of the second medical test of the subscriber are received without an indicator of the identity of the subscriber;
- store, in the data store, the results of the second medical test of the subscriber; and
- provide, to the party authorized by the subscriber, the results of the second medical test of the subscriber.

26. The system of claim 25, wherein the processing unit is configured to provide the results of the first medical test and rovide the results of the second medical test by display of both the results of the first medical test and the results of the second medical test, wherein display of the results of the first medical test includes display of indicator of the identity of the subscriber, and wherein display of the results of the second medical test includes display of a visual indicator indicating that the results of the second medical test of the subscriber are: (i) not linked to an indicator of the identity the subscriber and not verified, and (ii) an entity that provided a sample used for conducting the second medical test is not confirmed.

27. The system of claim 24, wherein the indicator of the identity of the subscriber is verified by the test agency that performed the medical test.

28. The system of claim 24, wherein the registry site verification information includes a digital certificate.

29. The system of claim 24, wherein the predefined type of medical test comprises a sexually transmitted disease screening test.

* * * * *